(12) United States Patent
Waller et al.

(10) Patent No.: US 9,526,657 B2
(45) Date of Patent: Dec. 27, 2016

(54) STRAP

(75) Inventors: Tom Waller, Nottingham (GB); Chris Johnson, Nottingham (GB)

(73) Assignee: SPEEDO INTERNATIONAL LIMITED, London (GB)

( * ) Notice: Subject to any disclaimer, the term of this patent is extended or adjusted under 35 U.S.C. 154(b) by 345 days.

(21) Appl. No.: 14/123,691

(22) PCT Filed: Jun. 1, 2012

(86) PCT No.: PCT/GB2012/051245
§ 371 (c)(1),
(2), (4) Date: Dec. 3, 2013

(87) PCT Pub. No.: WO2012/164302
PCT Pub. Date: Dec. 6, 2012

(65) Prior Publication Data
US 2014/0096313 A1     Apr. 10, 2014

(30) Foreign Application Priority Data
Jun. 3, 2011   (GB) .................................. 1109403.4

(51) Int. Cl.
| | | |
|---|---|---|
| *A61F 9/02* | (2006.01) | |
| *B63C 11/12* | (2006.01) | |
| *G02C 3/00* | (2006.01) | |
| *A63B 33/00* | (2006.01) | |

(52) U.S. Cl.
CPC ............... *A61F 9/027* (2013.01); *B63C 11/12* (2013.01); *G02C 3/003* (2013.01); *A63B 33/002* (2013.01)

(58) Field of Classification Search
CPC ............ A61F 9/027; A61F 9/04; A42B 3/228; A42B 3/14; A42B 3/20; A63B 71/10; A41F 1/00; B60P 7/0823; A44B 11/28; A44B 11/10; A44B 11/18
USPC ..... 2/452, 6.3, 417, 425, 9, 15; 24/301, 302, 24/310, 312, 196, 197, 200
See application file for complete search history.

(56) References Cited

U.S. PATENT DOCUMENTS

| | | | |
|---|---|---|---|
| 4,819,303 A | 4/1989 | Udelhofen | |
| 5,177,837 A * | 1/1993 | Rekuc ................... | A44B 11/00 24/198 |
| 5,566,427 A * | 10/1996 | Lathrop ................ | A44B 11/06 2/452 |

(Continued)

FOREIGN PATENT DOCUMENTS

| | | | | |
|---|---|---|---|---|
| DE | 29922975 U1 * | 7/2000 | ............. | A61F 9/027 |
| WO | WO 00/02505 | 1/2000 | | |

OTHER PUBLICATIONS

International Search Report for PCT/GB2012/051245 dated Aug. 10, 2012.

(Continued)

*Primary Examiner* — Tejash Patel
(74) *Attorney, Agent, or Firm* — Marvin Petry; Stites & Harbison PLLC

(57) ABSTRACT

The present invention provides a strap for securing a garment or article (e.g. swimming goggles) to a wearer's/user's body. The strap comprises a first portion (1) having a tensioner end (2), the tensioner end including and terminating at a tensioner (3). The strap further comprises a second portion (4) comprising a clip end (5), the clip end including and terminating at a clip (6). In use, the second portion passes through the tensioner and the clip is releasably securable onto the second portion.

15 Claims, 4 Drawing Sheets

(56) References Cited

U.S. PATENT DOCUMENTS

| | | | |
|---|---|---|---|
| 5,706,527 A | 1/1998 | Kita et al. | |
| 5,896,588 A | 4/1999 | Chiang | |
| 5,970,585 A * | 10/1999 | Scholey | A44B 11/006 |
| | | | 2/452 |
| 6,247,811 B1 | 6/2001 | Rhoades et al. | |
| 6,349,421 B2 * | 2/2002 | Fukasawa | 2/428 |
| 6,826,785 B2 * | 12/2004 | McNeal | A44B 11/12 |
| | | | 2/452 |
| 7,823,226 B2 * | 11/2010 | Chou | A44B 11/04 |
| | | | 2/448 |
| 7,966,701 B2 * | 6/2011 | Shiue | A61F 9/027 |
| | | | 2/452 |
| 2009/0133184 A1 | 5/2009 | Fukasawa | |

OTHER PUBLICATIONS

Written Opinion by They International Searching Authority for PCT/GB2012/051245 dated Aug. 10, 2012.

\* cited by examiner

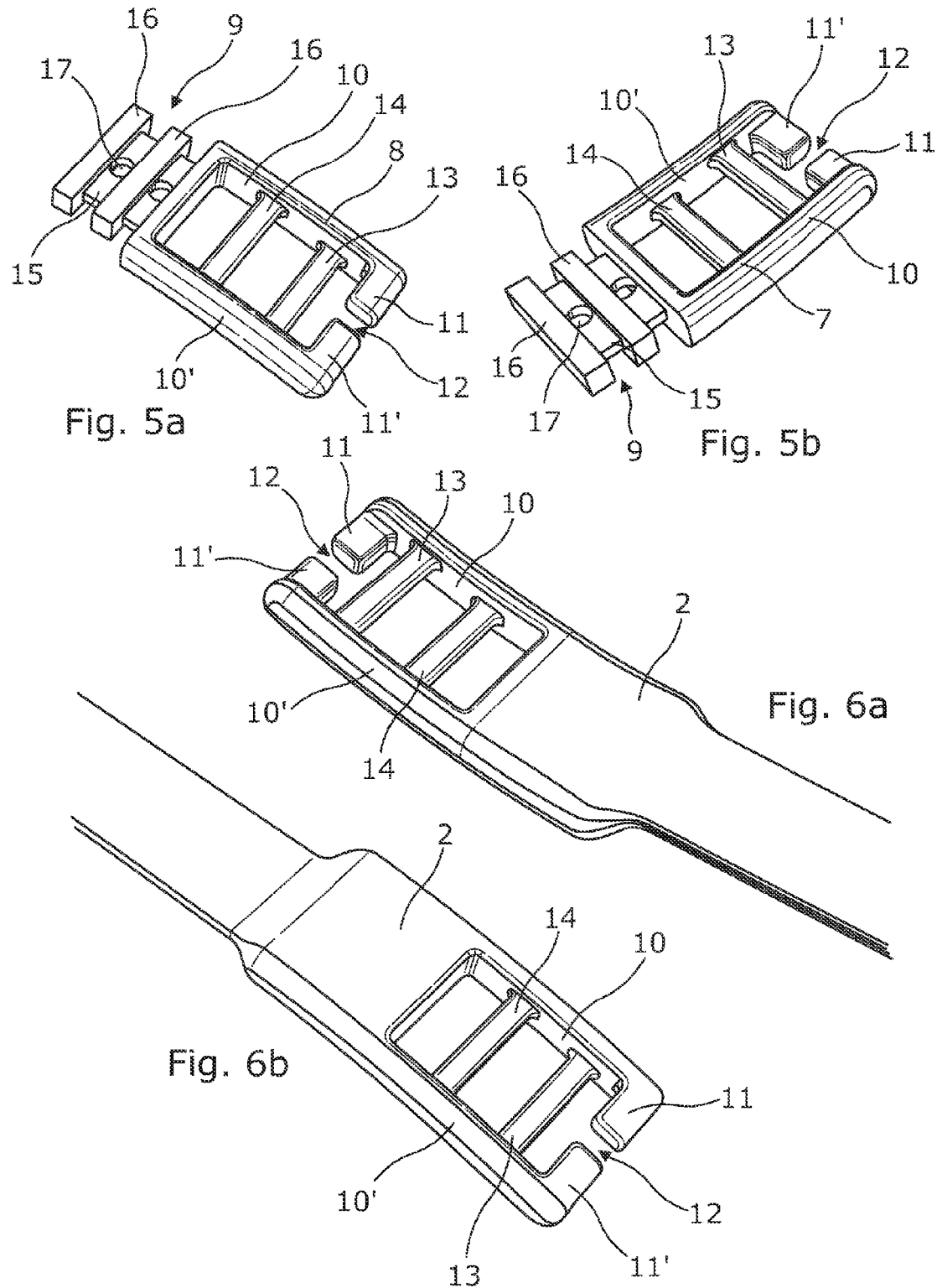

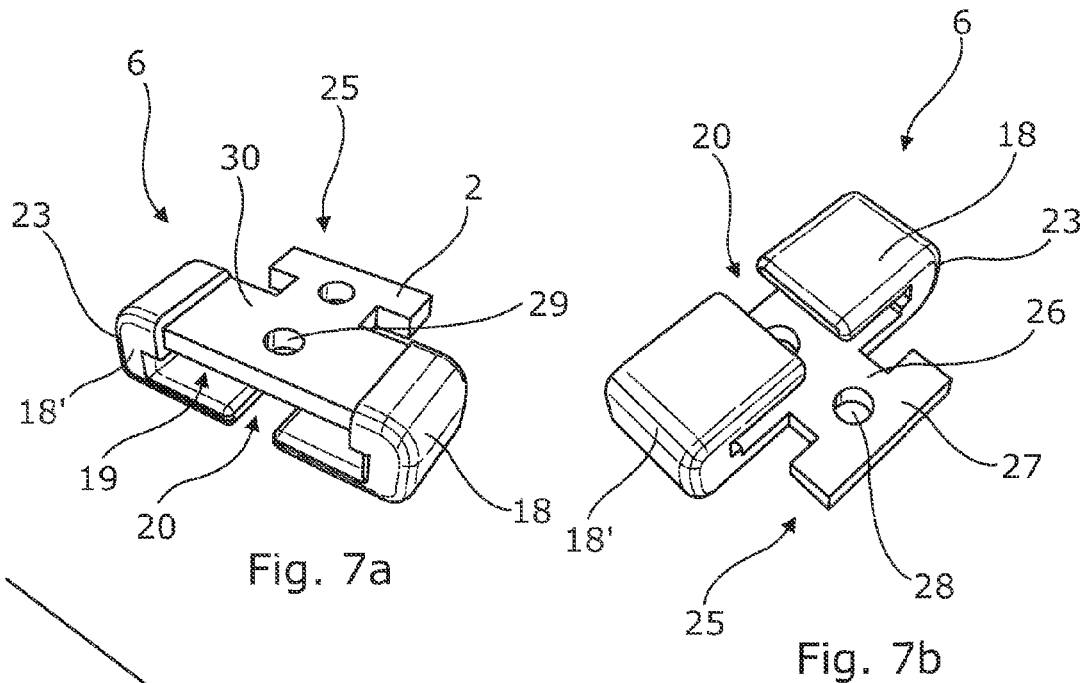
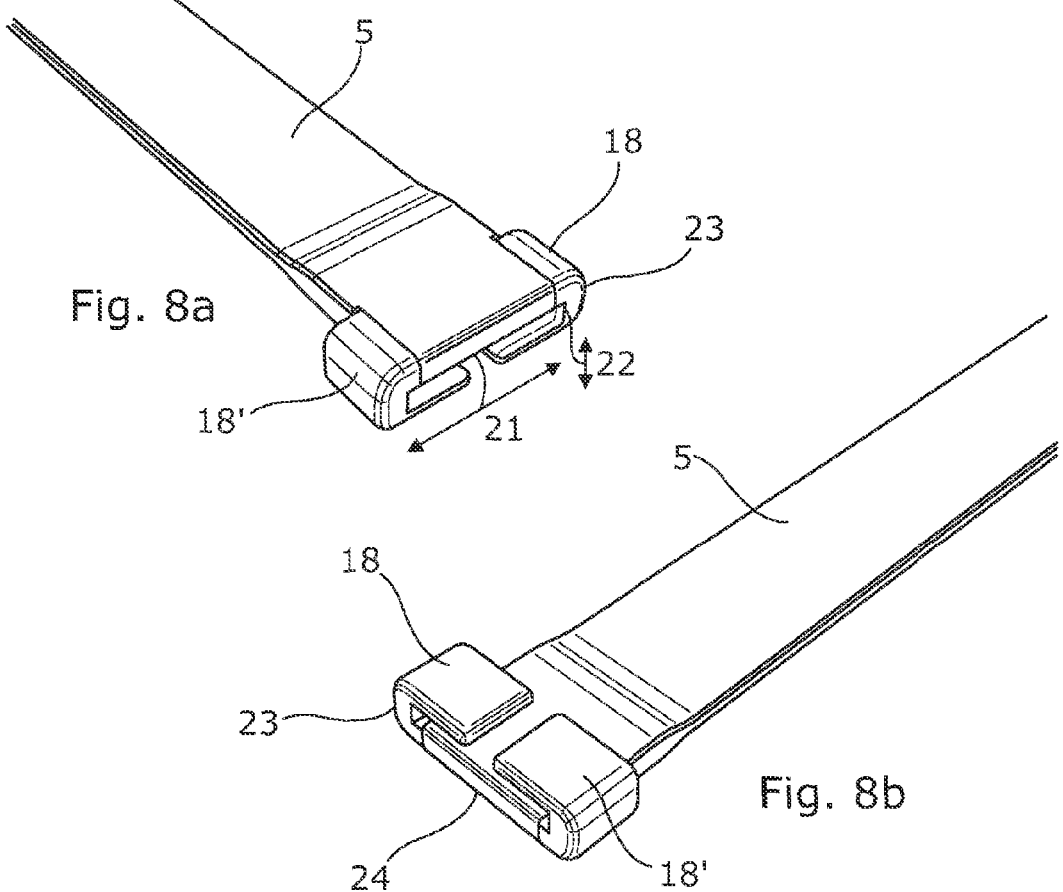

STRAP

FIELD OF THE INVENTION

This invention relates to a strap. In particular, this invention relates to a strap (or belt) which is useful for securing garments (e.g. sportswear) or articles (e.g. sporting articles such as hand paddles or kick fins) to a wearer's/user's body. Particularly preferred embodiments relate to a head strap for eyewear such as eyewear for safety and/or sporting purposes.

BACKGROUND

It is often desirable to secure eyewear to a wearer's head to avoid loss or movement of the eyewear. For eyewear (e.g. goggles or mask) which is worn in sporting activities such as swimming or skiing, it is especially important to secure the eyewear to the wearer's face and elastic head straps are typically used for this purpose.

Ideally these head straps need to be adjustable to cater for a range of head sizes and to allow the wearer to select their desired strap tension. One way of achieving this adjustability has been to provide a buckle through which the strap passes, the free end of the strap being pulled to tighten the head strap once the eyewear is in place. One problem with this adjustment arrangement is that the free end can cause discomfort and distraction by flapping around when the eyewear is in place.

Another problem with the known adjustment arrangements is that the buckle can protrude significantly from the back of the head when the eyewear is being worn. This can cause discomfort, especially if a tight fitting hat or cap is worn over the top of the strap. Furthermore, in the case of swimming goggles, the protrusion of the buckle can create frictional drag (whether or not the buckle is covered by a swimming cap) and this is undesirable.

Finally, once the strap is tightened, it can be difficult to readjust the tension in the strap for several reasons. Firstly, it is more difficult to loosen the head strap than it is to tighten it and it may be necessary to remove the eyewear in order to loosen the head strap. Secondly, if the wearer is participating in competitive sporting activities, it may only become apparent that the head strap is incorrectly adjusted once the competitive activity has commenced, by which time it will be too late to make any further adjustments. For this reason, it is desirable to provide some means for allowing a reliable and accurate measurement of tension within the head strap so that the wearer can ensure that the head strap is correctly adjusted.

SUMMARY OF THE INVENTION

In a first aspect, the present invention provides a strap for securing a garment/article (e.g. a sporting garment/article) to a wearer's/user's body, the strap comprising a first portion having a tensioner end, the tensioner end including and terminating at a tensioner, the tensioner having a lower surface which, in use, faces the wearer's body, an opposing upper surface and an attachment portion for attachment to said tensioner end, the strap further comprising a second portion comprising a clip end, the clip end being secured to and terminating at a clip, wherein, in use, the second portion passes through the tensioner and the clip is releasably securable onto the second portion at a position spaced from the clip end.

By providing a strap having two ends which terminate at a tensioner and a clip, the clip being releaseably securable to the second portion after the second portion has passed through the tensioner, any free ends which could flap around and cause discomfort and distraction are eliminated.

Preferably, the clip is releaseably securable onto the second portion (at a position spaced from the clip end) and moveable (e.g. by sliding) along the second portion. This allows any slack in the second portion between the tensioner and the clip end to be eliminated, again decreasing the possibility of discomfort and distraction.

Preferably, the strap is a head strap for eyewear, the tensioner having a lower surface which, in use, faces the wearers head.

In preferred embodiments, the upper and lower surfaces of the tensioner are curved into convex surfaces. Preferably they are curved into convex cylindrical surfaces. The radius of curvature is preferably 65-90 mm. More preferably, the radius of curvature is between 75-90 mm and most preferably between 84-88 mm. The radius of curvature is preferably selected so that it matches the curve of the rear of the average male $95^{th}$ percentile head. In this case, the radius of curvature is about 86 mm.

By providing curved convex upper and lower tensioner surfaces (which equates to providing a curved tensioner), it is possible to fit the tensioner to the wearer's body. Fitting a head strap tensioner to the wearer's head minimises discomfort should the wearer chose to wear a tight fitting hat or cap over the head strap. The curved tensioner also helps to reduce water resistance when used on swimming goggles because the tensioner does not protrude from the wearer's head.

In some embodiments, the tensioner comprises a frame formed of two arms extending from the attachment portion, wherein the ends of the arms distal the attachment portion each comprise a tooth, the teeth defining an opening distal the attachment portion, the teeth being closer to the upper surface of the tensioner than the lower surface, wherein the tensioner further comprises two cross bars extending between the arms and wherein the cross bar which is distal the attachment portion is closer to the lower surface of the tensioner than the upper surface.

This arrangement is provided to help minimise the profile of the tensioner (e.g. to reduce discomfort caused by a head strap when a tight-fitting hat/cap is worn and to reduce frictional resistance). In use, the second portion of the strap rests as a double layer against the teeth and the cross bar distal the attachment portion (whereas the second portion loops around the cross bar proximal the attachment portion so that only a single layer rests on each side of the proximal cross bar). The off-setting of the distal cross bar and the teeth helps to reduce any protrusion of the double layered second portion beyond the surfaces of the tensioner. The double layer of the second portion passes over the distal cross bar so positioning of the distal cross bar away from the upper surface helps to provide space in which the double layer can sit without protruding above the upper surface. The double layer of the second portion passes under the teeth so positioning of the teeth away from the lower surface (e.g. flush with the upper surface) helps to provide space in which the double layer can sit without protruding below the lower surface.

The cross bar proximal the attachment portion can be located midway between the upper and lower surfaces of the tensioner but preferably is off-set slightly towards the upper surface. This helps to facilitate insertion of the second portion into the tensioner.

Preferably the tensioner is formed of plastics material such as polycarbonate.

In preferred embodiments, the tensioner attachment portion comprises a tab having at least one rib extending across the width of the tab, the at least one rib having a greater width and/or depth than the tab. Preferably, the attachment portion comprises at least two ribs. More preferably, said tab further comprises at least one aperture.

The tab, rib(s) and apertures are provided to assist in attachment of the tensioner to the tensioner end of the strap. Preferably, the strap is formed of plastic material e.g. silicone which is molded (e.g. injection molded or compression molded) around the attachment portion. By providing the rib(s) and optionally, the aperture(s), it is possible to ensure a firm bond between the molded plastic material and the attachment portion.

Alternatively, the strap e.g. the silicone strap may be connected to the tensioner end of the first portion using some other connection means e.g. a snap fit connection.

Preferably, the clip comprises a pair of jaws defining a channel and an opening, the second portion of the strap being insertable into said channel through said opening to releasably secure the clip onto the second portion. The channel preferably has a cross section (e.g. a rectangular cross section) with a major dimension and a minor dimension, the major dimension of the cross-section substantially matching the width of the second section. This ensures a snug fit of the second portion in the channel which prevents inadvertent movement of the clip along the second portion.

Preferably, the minor side of the clip defining the minor dimension is small enough such that the minor side of the clip can pass through the tensioner between the side arms and between the two cross bars. Conversely, the major side of the clip defining the major dimension (which must at least match the width of the second portion of the strap) is, typically, larger than the distance between the tensioner side arms and cross bars so that the clip cannot pass through when the major side of the clip is presented. This arrangement allows the width of the tensioner (in the direction of the cross bars) to be reduced (which helps to reduce frictional drag and increase comfort for the wearer). The tensioner need only have a width sufficient to allow passage of the minor side of the clip and not the major side.

Preferably, the clip is formed of plastics material such as polycarbonate.

In preferred embodiments, the clip comprises an attachment portion having a tab with at least one rib extending across the width of the tab, the at least one rib having a greater width than the tab. More preferably, said tab further comprises at least one aperture. Additionally, or alternatively, an aperture may be provided on a recessed portion of the major side of the clip, the recessed portion being overlaid by the clip end of the strap.

The tab, rib and apertures are provided to assist in attachment of the clip to the clip end of the strap. Preferably, the strap is formed of plastic material e.g. silicone which is molded (e.g. injection molded or compression molded) around the clip attachment portion. By providing the rib and optionally, the aperture(s), it is possible to ensure a firm bond between the molded plastic material and the clip attachment portion.

Alternatively, the strap e.g. the silicone strap may be connected to the clip end of the second portion using some other connection means e.g. a snap fit connection.

In preferred embodiments, the second portion has indicia provided along at least a part of its length. The tensioner preferably includes a window in which at least one of said indicia on the second portion is visible when the strap is in use. The window is preferably defined by the side arms, the teeth and the attachment portion. By providing indicia on the second portion, it is possible to reliably reproduce a desired tension in the strap. For example, the wearer can fit a strap to the desired tension and then can observe the indicium framed by the tensioner window at the desired tension. The wearer then knows that, in order to recreate the desired tension, they can set the strap so that the same indicium is framed by the tensioner window.

The indicia may be visible and or tactile indicia. The indicia may be numerical indicia.

Preferably, the strap includes an indicator which helps to accurately position the desired indicium in the tensioner window. The indicator may be provided on the tensioner side arms, the tensioner attachment portion or on the first portion of the strap adjacent the tensioner. The indicator may be a linear or arrow-shaped element. It may be raised from, recessed into or printed onto the surface of the tensioner/first portion. By providing an indicator, the wearer can more accurately determine the required location of the desired indicium in the tensioner window.

Preferably, when the strap is a head strap, the first portion of the head strap has a first eyewear connection end opposite the tensioner end and the second portion of the head strap has a second eyewear connection end opposite the clip end. Most preferably, the first and second eyewear connection ends are connected to each other via a connection portion which, h, in use, passes round the rear of the wearer's head such that, in use, the first portion, second portion and connection portions form a double loop around the rear of the wearer's head. In this case, the present invention provides a one-piece double loop strap with integral tensioner and clip.

Preferably, the strap is a head strap is for sports eye wear such as a mask (e.g. for diving or skiing) or goggles (e.g. for swimming). Double loop straps (as described above) are especially desirable especially for sports eyewear used in competitive events such as swimming goggles.

Preferred embodiments of the present invention will now be described with reference to the accompanying figures in which:

BRIEF DESCRIPTION OF THE DRAWINGS

FIGS. 5a and 5b show top and bottom elevational views respectively of a tensioner;

FIGS. 6a and 6b show a bottom and top elevational view respectively of a tensioner/strap assembly;

FIGS. 7a and 7b show bottom and top elevational views respectively of a clip;

FIGS. 8a and 8b show a bottom and top elevational view respectively of a clip/strap assembly;

DETAILED DESCRIPTION OF THE INVENTION

Figure 1:
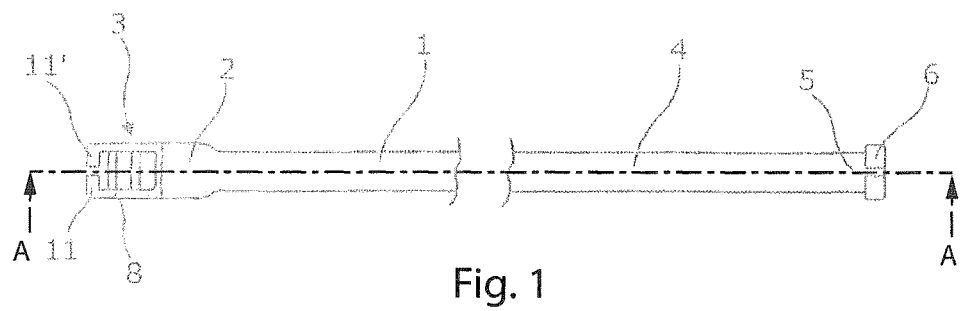
FIG. 1 shows a top view of a first embodiment of the present invention.
Figure 2:
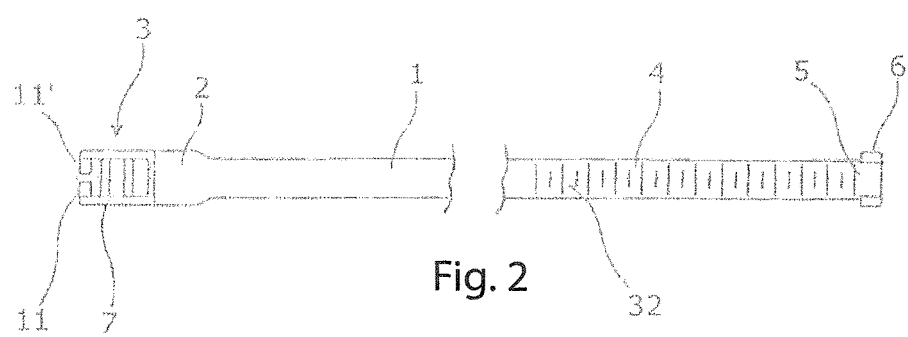
FIG. 2 shows a bottom view of the first embodiment of the present invention.

FIGS. 1, 2, 3 and 4 show a top, bottom, longitudinal cross section and side view of a head strap for swimming goggles. The head strap comprises a first portion 1 having a tensioner end 2. The tensioner end 2 includes and terminates at a tensioner 3 which is shown in more detail in FIGS. 5a, 5b, 6a and 6b. The head strap further comprises a second portion 4 which comprises a clip end 5. The clip end includes and terminates at a clip 6 which is shown in more detail in FIGS. 7a, 7b, 8a and 8b. The first and second portions 1, 4 are joined to one another via a connection portion (not shown). In use, the second portion 4 passes through the tensioner 3, and the clip 6 is releasably securable onto the second portion 4 as described below.

FIGS. 5a/b and 6a/b show a polycarbonate tensioner which is useful in the present invention. It has a lower surface 7 which, in use, faces the wearer's head and an opposing upper surface 8. It also includes an attachment portion 9 for attachment to the tensioner end 2.

The upper and lower surfaces 7, 8 of the tensioner 3 are curved into convex, cylindrical surfaces having a radius of curvature around 86 mm. The radius of curvature is selected so that it matches the curve of the rear of the average male $95^{th}$ percentile head. This curved profile improves the fitting of the tensioner to the wearer's head so that discomfort is minimised should the wearer chose to wear a tight fitting hap or cap over the head strap.

The tensioner comprises a frame formed of two arms 10, 10' extending from the attachment portion 9. The ends of the arms distal the attachment portion each comprise a tooth 11, 11'. The teeth define an opening 12 distal the attachment portion 9. The teeth 11, 11' are closer to the upper surface 8 of the tensioner 3 than the lower surface 7. The tensioner further comprises two cross bars, 13, 14 extending between the arms 10, 10". The cross bar 13 which is distal the attachment portion 9 is closer to the lower surface 7 of the tensioner 3 than the upper surface 8. The cross bar 14 proximal the attachment portion 9 can be located midway between the upper and lower surfaces 7, 8 of the tensioner but preferably is off-set slightly towards the upper surface 8. This arrangement helps minimise the profile of the tensioner when the second portion has been passed through it as described below.

Figure 3:
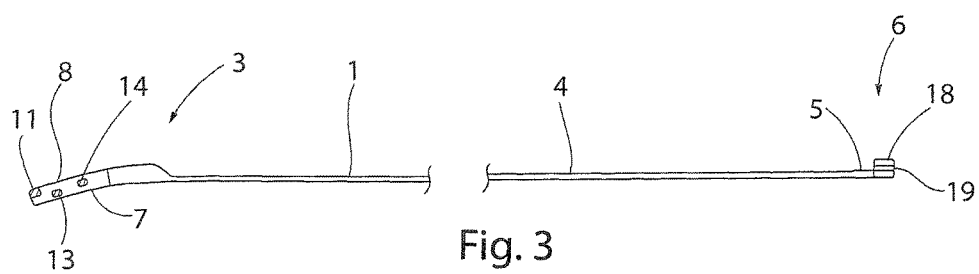
FIG. 3 shows a longitudinal cross section along line A-A of FIG. 1.
Figure 4:
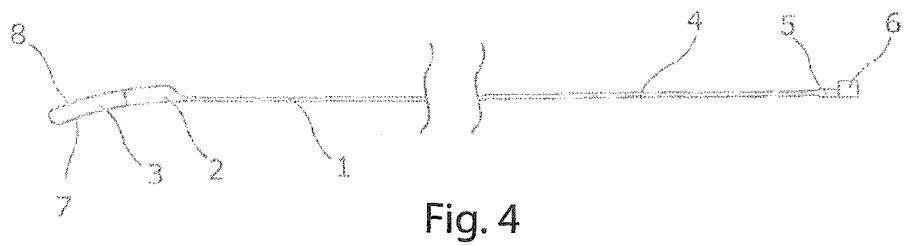
FIG. 4 shows a side view of the first embodiment of the present invention.

The tensioner attachment portion 9 (shown in FIGS. 5a and 5b) comprises a tab 15 having two ribs 16 extending across the width of the tab 15. The ribs have a greater width and depth than the tab 15. The tab also comprises two apertures 17. The tab 15, ribs 16 and apertures 17 are provided to assist in attachment of the tensioner 3 to the tensioner end 2 of the head strap. The head strap is formed of plastic material e.g. silicone which is molded (e.g. injection molded or compression molded) around the attachment portion 9 as shown in FIGS. 6a and 6b. By providing the ribs and apertures, it is possible to ensure a firm bond between the molded plastic material of the tensioner end 2 and the attachment portion 9. FIG. 3 shows how the cross bars 13, 14 are embedded within the plastics material forming the tensioner end 2.

FIGS. 7a/b and 8a/b show a polycarbonate clip 6 which is useful in the present invention. The clip 6 comprises a pair of jaws 18, 18' defining a channel 19 and an opening 20. The second portion 4 of the head strap is insertable into the channel 19 through the opening 20 to releasably secure the clip 6 onto the second portion 4. The channel has a rectangular cross section with a major dimension 21 and a minor dimension 22, the major dimension 21 of the cross-section substantially matching the width of the second section.

This ensures a snug fit of the second portion in the channel which prevents inadvertent movement of the clip along the second portion.

The minor side 23 of the dip 6 defining the minor dimension 22 is small enough such that the minor side of the dip can pass through the tensioner 3 between the side arms 10, 10', between the two cross bars 13, 14 and between the cross bar 14 proximal the attachment portion and the attachment portion 9. Conversely, the major side 24 of the clip 6 defining the major dimension 21 (which must at least match the width of the second portion 4 of the head strap) is, typically, larger than the distance between the tensioner side arms 10, 10', cross bars 13, 14 and cross bar 14 and the attachment portion so that the clip 6 cannot pass through when the major side of the dip is presented. This arrangement allows the width of the tensioner (in the direction of the cross bars) to be reduced (which helps to reduce frictional drag and increase comfort for the wearer. The tensioner needs only have a width sufficient to allow passage of the minor side of the clip and not the major side.

The clip comprises an attachment portion 25 having a tab 26 with a rib 27 extending across the width of the tab, the rib having a greater width than the tab. The tab further comprises an aperture 28 and another aperture 29 is provided on a recessed portion 30 of the clip.

The tab, rib and apertures are provided to assist in attachment of the clip 6 to the clip end 5 of the head strap. The head strap is formed of plastic material e.g. silicone which is molded (e.g. injection molded or compression molded) around the clip attachment portion 25 and the recessed portion 30 of the clip. By providing the rib and apertures, it is possible to ensure a firm bond between the molded plastic material and the clip 6.

Figure 9:
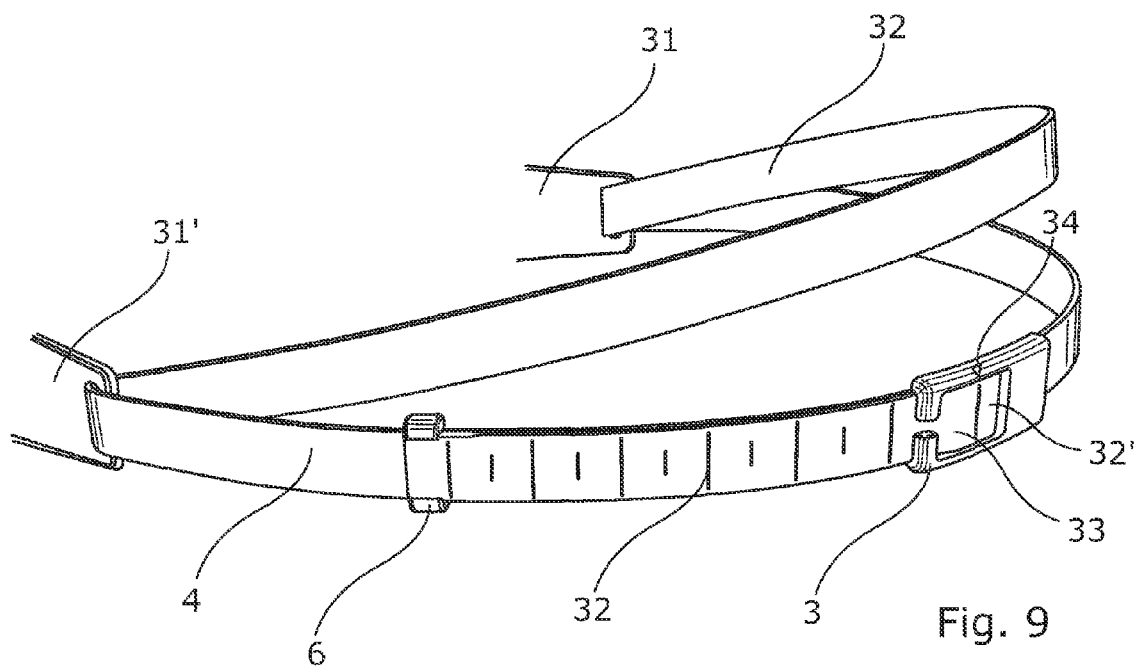
FIG. 9 shows the head strap of the first embodiment assembled with goggle head strap supports.

In use, the head strap is initially connected to swimming goggles by passing the clip 6 and the clip end 5 through an aperture provided in a first head strap support 31 followed by an aperture provided in a second head strap support 31'. These apertures are dimensioned to only receive the minor side 23 of the clip 6 in order to minimise dimensional height of the head strap supports, 31, 31'. Passing the clip 6 and clip end 5 through the head strap support apertures results in a loop 32 of strap (the connection portion) extending between the two head strap supports 31, 31' as shown in FIG. 9. The tensioner end 2 of the strap remains to one side of the first head strap support 31 and the clip end 5 of the strap to the opposite side of the second head strap support 31'.

The following steps are then carried out:

1) The clip 6 and clip end 5 are then passed through the tensioner 3 between the teeth 11, 11' and the cross bar 13 distal from the attachment portion. The clip is passed through from the lower surface 7 towards the upper surface 8 on its side as only the minor side 23 can fit between the teeth and cross bar.

2) The clip 6 and clip end 5 are then passed through the tensioner 3 between the cross bar 13 distal from the attachment portion and the cross bar 14 proximal the attachment portion. The clip is passed through from the upper surface 8 towards the lower surface 7 on its side as only the minor side 23 can fit between the cross bars.

3) The clip 6 and clip end 5 are then passed through the tensioner 3 between the cross bar 14 proximal the attachment portion and the attachment portion 9. The clip is passed through from the lower surface 7 towards the upper surface 8 on its side as only the minor side 23 can fit between the cross bar and the attachment portion.

4) The second portion 4 of the strap proximal the clip end 5 is then looped back over the cross bar 14 proximal the attachment portion 9 and is inserted through the opening 12 to pass under the teeth 11, 11'. This results in the clip end 5 being looped back onto the second portion 4 of the head strap as shown in FIG. 10.

Figure 10:
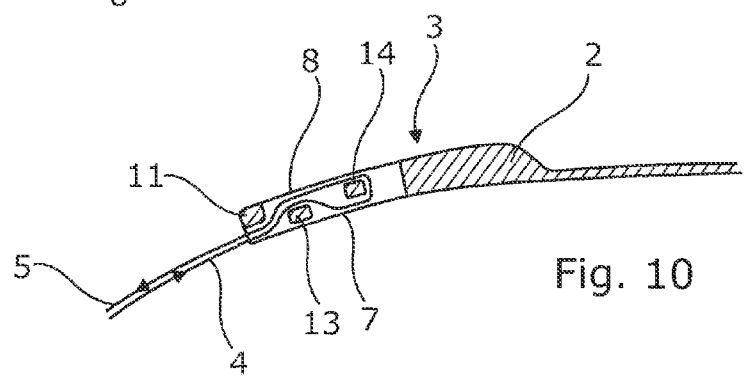
FIG. 10 shows a cross section through the tensioner when the first embodiment is assembled.

As shown in FIG. 10 the arrangement of the tensioner teeth 11, 11' and the cross bars 13, 14 helps to minimise the profile of the tensioner (which reduces discomfort when a tight-fitting hat/cap is worn and reduces frictional resistance). It can be seen that the second portion 4 of the head strap rests as a double layer against the teeth 11, 11' and the cross bar 13 distal the attachment portion whereas the second portion 4 loops around the cross bar 14 proximal the attachment portion 9 so that only a single layer rests on each side of the proximal cross bar 14. The off-setting of the distal cross bar 13 and the teeth 11, 11' helps to reduce any protrusion of the double layered second portion 4 beyond the surfaces 7, 8 of the tensioner 3. The double layer of the second portion 4 passes over the distal cross bar 13 so positioning of the distal cross bar 13 away from the upper surface 8 helps to provide space in which the double layer can sit without protruding above the upper surface 8. The double layer of the second portion 4 passes under the teeth 11, 11' so positioning of the teeth away from the lower surface 7 helps to provide space in which the double layer can sit without protruding below the lower surface 7.

As can be seen in FIG. 9, the clip is secured onto the second portion 4 remote from the clip end by inserting the second portion 4 into the channel 19 through the opening 20.

By providing a head strap having two ends which terminate at a tensioner 3 and a clip 6, the clip 6 being releaseably securable to the second portion 4 after the second portion has passed through the tensioner 3, any free ends which could flap around and cause discomfort and distraction are eliminated.

The clip 6 is releaseably securable onto and moveable by sliding along the second portion 4. This allows any slack in the second portion 4 between the tensioner 3 and the clip end 5 to be eliminated, again decreasing the possibility of discomfort and distraction. This movement is also desirable to help adjustment of the tension of the head strap as explained below.

The second portion 4 has visible indicia 32 provided along at least a part of its length on the underside. The tensioner 3 includes a window 33 in which at least one of said indicia 32 on the second portion 4 is visible when the head strap is in use. The window is defined by the side arms 10, 10', the teeth 11, 11' and the attachment portion 9. By providing indicia 32 on second portion, it is possible to reliably reproduce a desired tension in the head strap. The wearer can fit the head strap to the desired tension and then can observe the indicium 32' framed by the tensioner window at the desired tension. The wearer then knows that, in order to recreate the desired tension, they can set the head strap so that the same indicium 32' is framed by the tensioner window 33.

The tensioner includes an indicator 34 which helps to accurately position the desired indicium 32' in the tensioner window 33. The indicator is an arrow-shaped element. It is raised from the upper surface 8 of the tensioner. By providing an indicator 34, the wearer can more accurately determine the required location of the desired indicium 32' in the tensioner window 33.

The invention claimed is:

1. A strap for securing a sporting garment or article to a wearer's/user's body, the strap comprising a first portion having a tensioner end, the tensioner end including and terminating at a tensioner, the tensioner having a lower surface which, in use, faces the wearer's body, an opposing upper surface and an attachment portion for attachment to said tensioner end, the strap further comprising a second portion comprising a clip end, the clip end being secured to and terminating at a clip, wherein, in use, the clip and part of the second portion passes through the tensioner and is releasably securable to another part of the second portion which has not passed through the tensioner.

2. A strap according to claim 1 wherein the clip is moveable along the second portion.

3. A strap according to claim 1 wherein the strap is constructed to secure eyewear to a wearer's head, the tensioner having a lower surface which, in use, faces the wearer's head.

4. A strap according to claim 1 wherein the upper and lower surfaces of the tensioner are convex and concave surfaces, respectively.

5. A strap according to claim 4 wherein the upper and lower surfaces have a radius of curvature matching the radius of curvature of the rear of the 95$^{th}$ percentile of a male's head.

6. A strap according to claim 4 wherein the upper and lower surfaces have a radius of curvature of 65 mm-90 mm.

7. A strap according to claim 5 wherein the upper and lower surfaces have a radius of curvature of around 86 mm.

8. A strap according to claim 3 wherein the first portion has a first eyewear connection end opposite to said tensioner end and the second portion has a second eyewear connection end opposite the clip end and wherein the first and second eyewear connection ends are joined by a connection portion which, in use, passes around the rear of the wearer's head.

9. A strap according to claim 1 wherein the tensioner comprises two arms extending from the attachment portion, wherein the ends of the arms distal the attachment portion each comprise a tooth, the teeth defining an opening distal the attachment portion, the teeth being closer to the upper surface of the tensioner than the lower surface, wherein the tensioner further comprises two cross bars extending between the arms and wherein the cross bar which is distal the attachment portion is closer to the lower surface of the tensioner than the upper surface.

10. A strap according to claim 1 wherein the attachment portion comprises a tab having at least one rib extending across the width of the tab, the at least one rib having a greater width and/or depth than the tab.

11. A strap according to claim 10 wherein the attachment portion comprises at least two ribs.

12. A strap according to claim 10 wherein said tab further comprises at least one aperture.

13. A strap according to claim 1 wherein the clip comprises a pair of jaws defining a channel and an opening, the second portion of the strap being insertable into said channel through said opening to releasably secure the clip onto the second portion.

14. A strap according to claim 1 wherein the second portion has indicia provided along at least a part of its length, wherein, in use, the second portion passes through the tensioner, the tensioner including a window in which at least one of said indicia on the second portion is visible.

15. Swimming goggles or mask having a strap according to claim 1.

* * * * *